US007777392B2

(12) United States Patent
Chen et al.

(10) Patent No.: US 7,777,392 B2
(45) Date of Patent: Aug. 17, 2010

(54) CONTOURED THERMOMECHANICAL ACTUATORS AND PULSING FOR ENHANCED DYNAMIC PERFORMANCE

(75) Inventors: Shih-Chi Chen, Boston, MA (US); Martin L. Culpepper, Danvers, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 317 days.

(21) Appl. No.: 11/937,224

(22) Filed: Nov. 8, 2007

(65) Prior Publication Data
US 2009/0058222 A1     Mar. 5, 2009

Related U.S. Application Data

(60) Provisional application No. 60/970,158, filed on Sep. 5, 2007.

(51) Int. Cl.
*H02N 10/00*     (2006.01)
(52) U.S. Cl. ................ 310/306; 60/527; 318/117
(58) Field of Classification Search ......... 310/306, 310/307; 60/527, 528; 318/116, 117
See application file for complete search history.

(56) References Cited

U.S. PATENT DOCUMENTS

| 3,389,314 | A  | * | 6/1968  | Lewis ................... 318/117 |
| 6,164,837 | A  |   | 12/2000 | Haake et al.                     |
| 6,338,249 | B1 | * | 1/2002  | Pai et al. ................ 60/528 |
| 6,460,972 | B1 | * | 10/2002 | Trauernicht et al. ...... 347/54 |
| 6,464,341 | B1 | * | 10/2002 | Furlani et al. ........... 347/54 |
| 6,827,428 | B2 | * | 12/2004 | Silverbrook ............. 347/60 |
| 6,982,515 | B2 | * | 1/2006  | Howell et al. ........... 310/307 |
| 7,033,000 | B2 | * | 4/2006  | Delametter et al. ........ 347/56 |
| 7,451,596 | B2 | * | 11/2008 | Culpepper et al. ......... 60/527 |
| 2008/0278545 | A1 | * | 11/2008 | Sheahan et al. ......... 347/57 |
| 2009/0058222 | A1 | * | 3/2009  | Chen et al. ............. 310/306 |

OTHER PUBLICATIONS

Jeffery T. Bulter et al., "Average Power Control and Positioning of Polysilicon Thermal Actuator", Sensors and Actuators, 72 (1999) 88-97.*
Chen et al., "Design and Optimization of Thermomechanical Actuator via Contour Shaping", Proceedings of IMECE 2005, ASME International Mechanical Engineering Congress and Exposition, Nov. 5-11, 2005 Orlando, FL, USA IMEDE2005-79780.*
Chen, S.-C., "A six-degree-of-freedom compliant micro-manipulator for Silicon Optical Bench", S.M. thesis, Dept. of Mech. Eng., MIT 2003. pp. 1-8.
Jokiel, B., Benavides, G. L., Bieg, L. F., and Allen, J. J., "Planar and spatial three-degree-of-freedom micro-stages in silicon MEMS," Annual Meeting of the American Society for Precision Engineering, 2001, pp. 32-35.

(Continued)

*Primary Examiner*—Karl I Tamai
(74) *Attorney, Agent, or Firm*—Sampson+Associates, P.C.

(57) ABSTRACT

A thermomechanical actuation system and method includes an elongated thermomechanical actuator (TMA), which is contoured so that electrical resistance at a mid-portion of the TMA is less than at end portions thereof. A pulse generator is electrically coupled to the TMA, and is configured to supply excitation pulses to the TMA. The excitation pulses are transient, so that each pulse is terminated prior to reaching a steady state amplitude, while having sufficient energy to heat the TMA to its predetermined operational temperature range.

25 Claims, 18 Drawing Sheets

TRANSIENT TEMPERATURE RESPONSE (DASHED LINE) ON THE TIP OF A CONTOURED CHEVRON TMA WITH CONVENTIONAL SIGNAL (TOP) AND SHORT PULSES (BOTTOM)

OTHER PUBLICATIONS

Bamberger, H. and Shoham, M., "A new configuration of a six degree-of-freedom parallel robot for MEMS fabrication," Proc. IEEE International Conference on Robotics and Automation, 2004, pp. 4545-4550.

Liu, Z., DeVoe, D. L., "Micromechainsm fabrication using silicon fusion bonding," Robotics and Computer Integrated Manufacturing, 2001, Elsevier Science Ltd., pp. 131-137.

Hart, Anastasios John, Lucas van Laake, and Alexander H. Slocum, "Desktop Growth of Carbon-Nanotube Monoliths with In Situ Optical Imaging", 2007 Wiley-VCH Verlag Gmbh & Co., KGaA,Weinheim, small 2007, 3, No. 5, 772-777.

Chen,J. S. et al., "Design of a High-speed, Micro-scale Fast Scanning Stage for Two-photon endomicroscopy," Proceedings of the Annual Meeting of the ASPE, Monterey, CA, Oct. 2006, pp. 279-282.

Choi, H., Chen, S., et al., "Design of a Non-linear Endomicroscope Biopsy Probe," OSA Biomedical Optics Topical Meeting and Tabletop Exhibit, FL, Mar. 19-23, 2006, 3 pages.

Chen S., and M. L. Culpepper, "Design of Contoured Microscale Thermomechanical Actuators," Institute of Physics Publishing, Journal of Microelecromechanical Systems, vol. 15, No. 5,Oct. 2006, pp. 1226-1234.

Yoon, Dae Sung, You-Seop Lee, Youngsun Lee, Hye Jung Cho, Su Whan Sung, Kwang W. Oh, Junhoe Cha and Geunbae Lim, "Precise temperature control and rapid thermal cycling in a micromachined DNA polymerase chain reaction chip", Journal of Micromechanics and Microengineering,2002 IOP Publishing Ltd., pp. 813-823.

DeVoe,Don L., "Thermal Issues in MEMS and Microscale Systems", IEEE Transactions on Components and Packaging Technologies, vol. 25, No. 4, Dec. 2003, pp. 576-583.

Bechtold, Tarmara, Evgenii B. Rudnyi and Jan G. Korvink, "Dynamic electro-thermal simulation of microsystems-a review", Journal of Micromechanics and Microengineering,(2005) IOP Publishing,Ltd, pp. R17-R31.

Chen, S. and Culpepper, M. L., "Design of a Six-axis Microscale Nano-positioner—μHexflex", 2005 Elsevier Inc., Journal of Precision Engineering, 2006, vol. 30, Issue 3, p. 315-324.

Carl, P., "Design of a Thermally Actuated Silicon Optical Bench Mount for Obtaining and Maintaining GRIN Lens Focus in a Two-photon Endoscope", M.S. Thesis, Dept. of Mechanical Engineering, Technischen Universitat Munchen, 2004, pp. 1-86.

Guckel, H., J. Klein, T. Christenson, K. Skrobis, M. Laudon, E. G. Lovell, "Thermo-magnetic metal flexure actuators," 1992, Solid-State Sensor and Actuator Workshop, 5th Technical Digest, IEEE, pp. 73-75.

Que, L., J. -S. Park, Y. B. Gianchandani, "Bent-beam electro-thermal actuators for high force applications,", 1999, Microelectromechanical systems (MEMS), IEEE International Conference, pp. 31-36.

* cited by examiner

TRANSMISSION RATIO SURFACE PLOT AS A FUNCTION OF $\theta_1$, $\theta_2$, AND THE NUMBER OF PARALLEL TMAs

CONTOURED THERMOMECHANICAL ACTUATORS AND PULSING FOR ENHANCED DYNAMIC PERFORMANCE

RELATED APPLICATION

This application claims the benefit of U.S. Provisional Application Ser. No. 60/970,158, entitled High Speed Pulsing Technique for Non-uniform Heat Generation Thermal System, filed on Sep. 5, 2007, the contents of which are incorporated herein by reference in their entirety for all purposes.

GOVERNMENT SPONSORSHIP

This invention was made with government support under Contract Number DMI-0348242, awarded by the National Science Foundation, and Contract Number I-R21-CA118400-01, awarded by the National Cancer Institute/National Institute of Health. The government has certain rights in the invention.

BACKGROUND

1. Technical Field

This invention relates to thermomechanical actuators, and more particularly to a system and method which uses pulsed actuation of contoured thermomechanical actuators for enhanced dynamic performance.

2. Background Information

A wide variety of thermomechanical actuators (TMAs) are known in the art. TMAs make use of Joule heating and thermal expansion of materials to generate displacements. Conventional TMAs, which contain slender, constant cross-section microfabricated beams, are well-known for their relatively large force and stroke outputs. Their bandwidths, however, are limited by the heat diffusion process. FIGS. 1A & 1B show common TMA configurations, including constant cross-section beam 30 disposed in parallel beam (FIG. 1A) and chevron (FIG. 1B) configurations. Due to their force/stroke characteristics and ease-of-fabrication, TMAs are frequently found in a variety of meso-/micro-scale devices and positioning systems, such as disclosed in U.S. patent application Ser. No. 11/037,866 (the '866 application), entitled Multiple Degree of Freedom Micro Electro-Mechanical System Positioner and Actuator, filed on Jan. 18, 2005, and which is fully incorporated herein. For instance, they have been used in in-package active fiber alignment devices, micro-scanners used in endoscopes, and meso-/micro-scale nanopositioners. However, drawbacks associated with conventional straight beam TMAs include relatively high power consumption, low efficiency, and low bandwidth, all of which tend to make it difficult to use these TMAs as the basis of practical and efficient devices.

Therefore, there are a number of unresolved issues associated with the use of TMAs, which are addressed by the present invention.

SUMMARY

In one aspect of the present invention, a thermomechanical actuation system includes an elongated thermomechanical actuator (TMA), which is contoured so that electrical resistance at a mid-portion of the TMA is lower than at end portions thereof. A pulse generator is electrically coupled to the TMA, and is configured to supply excitation pulses to the TMA. The excitation pulses are transient, so that each pulse is terminated prior to reaching a steady state amplitude, while having sufficient energy to heat the TMA to its predetermined operational temperature range.

In another aspect of the invention, a method of thermomechanical actuation includes providing an elongated thermomechanical actuator (TMA), having a contour, wherein electrical resistance at a mid-portion of the TMA is lower than at end portions thereof. The method further includes electrically coupling a pulse generator to the TMA, configuring the pulse generator to supply excitation pulses to the TMA, and configuring the excitation pulses to be transient, so that each pulse is terminated prior to reaching a steady state amplitude. The excitation pulses are provided with sufficient energy to heat the TMA to its predetermined operational temperature range.

The features and advantages described herein are not all-inclusive and, in particular, many additional features and advantages will be apparent to one of ordinary skill in the art in view of the drawings, specification, and claims. Moreover, is should be noted that the language used in the specification has been principally selected for readability and instructional purposes, and not to limit the scope of the inventive subject matter.

DETAILED DESCRIPTION

Figure 1A:
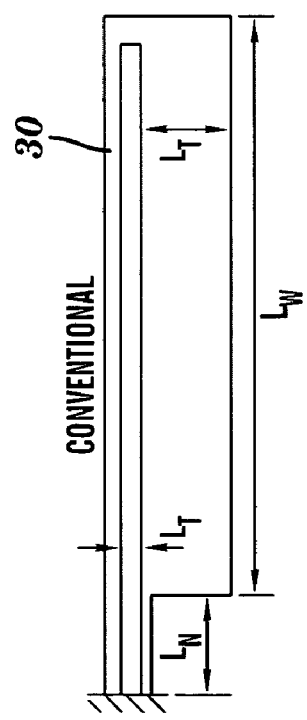
FIGS. 1A-1B are schematic plan views of configurations of straight beam TMAs of the prior art.

In the following detailed description, reference is made to the accompanying drawings that form a part hereof, and in which is shown by way of illustration, specific embodiments in which the invention may be practiced. These embodiments are described in sufficient detail to enable those skilled in the art to practice the invention, and it is to be understood that other embodiments may be utilized. It is also to be understood that structural, procedural and system changes may be made without departing from the spirit and scope of the present invention. The following detailed description is, therefore, not to be taken in a limiting sense, and the scope of the present invention is defined by the appended claims and their equivalents. For clarity of exposition, like features shown in the accompanying drawings are indicated with like reference numerals and similar features as shown in alternate embodiments in the drawings are indicated with similar reference numerals.

Where used in this disclosure, the term "axial" when used in connection with an element described herein, refers to a direction relative to the element, which is substantially parallel to its longitudinal dimension. Similarly, the terms "transverse" or "lateral" refer to a direction other than substantially parallel to the axial direction. The term "transverse cross-section" refers to a cross-section taken along a transverse plane. Moreover, for convenience, the term "TMA" refers to the driving beam of a TMA actuator, i.e., to the Joule heated beam of a particular TMA actuator configuration, with the understanding that such a Joule heated beam may be used in conjunction with other components that may include either constant cross-section beams (of relatively thick or thin transverse cross-section), or contoured beams, to form a TMA actuator such as shown in FIGS. 1D and 1E.

Figure 1B:
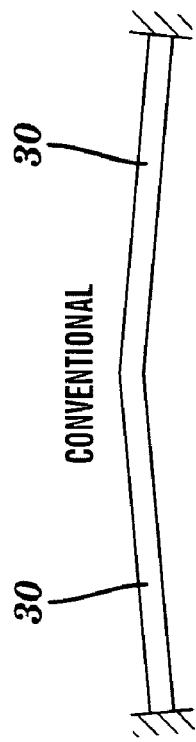
Figure 1C:
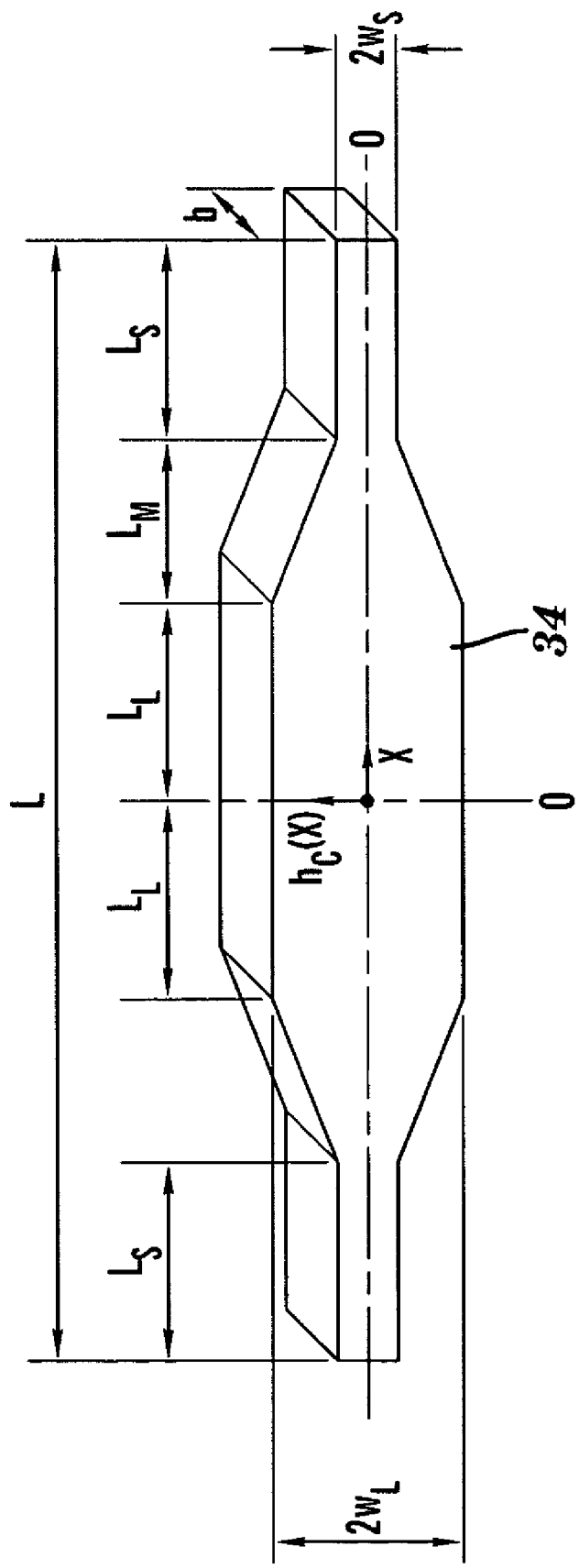
FIGS. 1C-1E are schematic plan views of contoured TMAs of the type used in embodiments of the present invention.
Figure 1D:
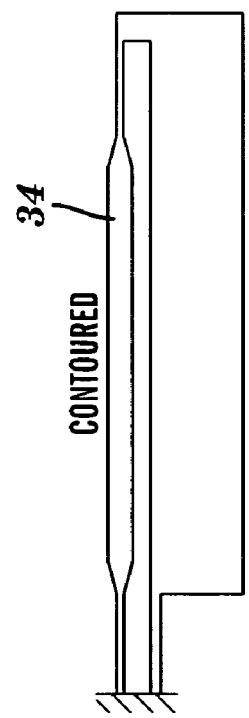
Figure 1E:
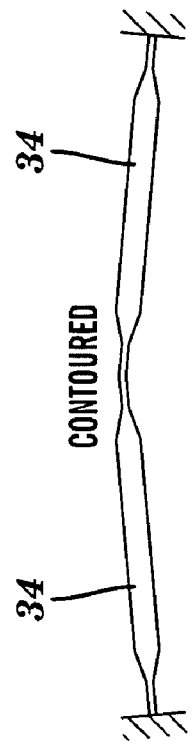

Referring to FIGS. 1C-1E, embodiments of the present invention include a contoured TMA 34 (FIG. 1C), which may be used in nominally any configuration, such as in parallel beam (FIG. 1D) or chevron (FIG. 1E) arrangements. As discussed in the aforementioned '866 application, such contouring may significantly reduce the drawbacks associated with conventional straight beam TMAs, particularly when used in conjunction with the short pulse actuation of the present invention, as will be discussed in greater detail hereinbelow.

It is to be noted that the concept of TMA contouring involves varying the electrical resistance (e.g., by varying the transverse cross-section as shown, and/or by varying the structural composition) of a TMA over its length. Although geometric contouring is shown and discussed herein as a desired approach for use in many applications, nominally any type of contouring may be used to vary the resistance of a TMA along its length. For example, TMAs may be contoured electrically, instead of, or in addition to, the aforementioned geometric approaches. This may be accomplished by adding dopants (e.g., ion implantation) during microfabrication of the beam to vary the structural composition of the TMA along its length. In this manner, the TMA may be fabricated to have higher electrical resistivity at end portions of the beam, relative to the electrical conductivity at a mid portion of the beam, with or without any geometric contour. A solely electrically contoured TMA (i.e., one without a geometric contour), may provide many, if not all, of the advantages provided by the geometrically contoured embodiments, particularly when used in applications such as on-chip chemical reactors that have few moving parts.

It has been established by the instant inventors that in many (e.g., quasi-static) applications, embodiments of contoured TMA 34 may simultaneously produce more than twice the force and stroke of an otherwise similar conventional TMA 30 of a constant cross-section. The inventors have found that this phenomenon may be due to the constant cross-section beam 30 being relatively inefficient at transforming thermal strain into mechanical energy, e.g., due to its storage of relatively high amounts of the strain energy. The inventors have further found that by contouring a beam, one may increase the thermal strain and elastic range of the beam while decreasing the strain energy that is stored (particularly when using geometric contouring as discussed above) in the beam during actuation. As a result, more energy is available to do useful work. Table 1 summarizes the performance improvements of a TMA 34 in a chevron configuration (as shown in FIG. 1E) relative to an otherwise similar constant cross-section TMA in a chevron configuration (FIG. 1B).

TABLE 1

Review of static performance improvements by contouring.

| Constant power | | Constant Stroke | |
|---|---|---|---|
| Stroke | Force | Power | Temperature |
| 4X | 2.5X | 65% | 35% |

Transient Heating Behavior of a Contoured Beam/TMA

Figure 2A:
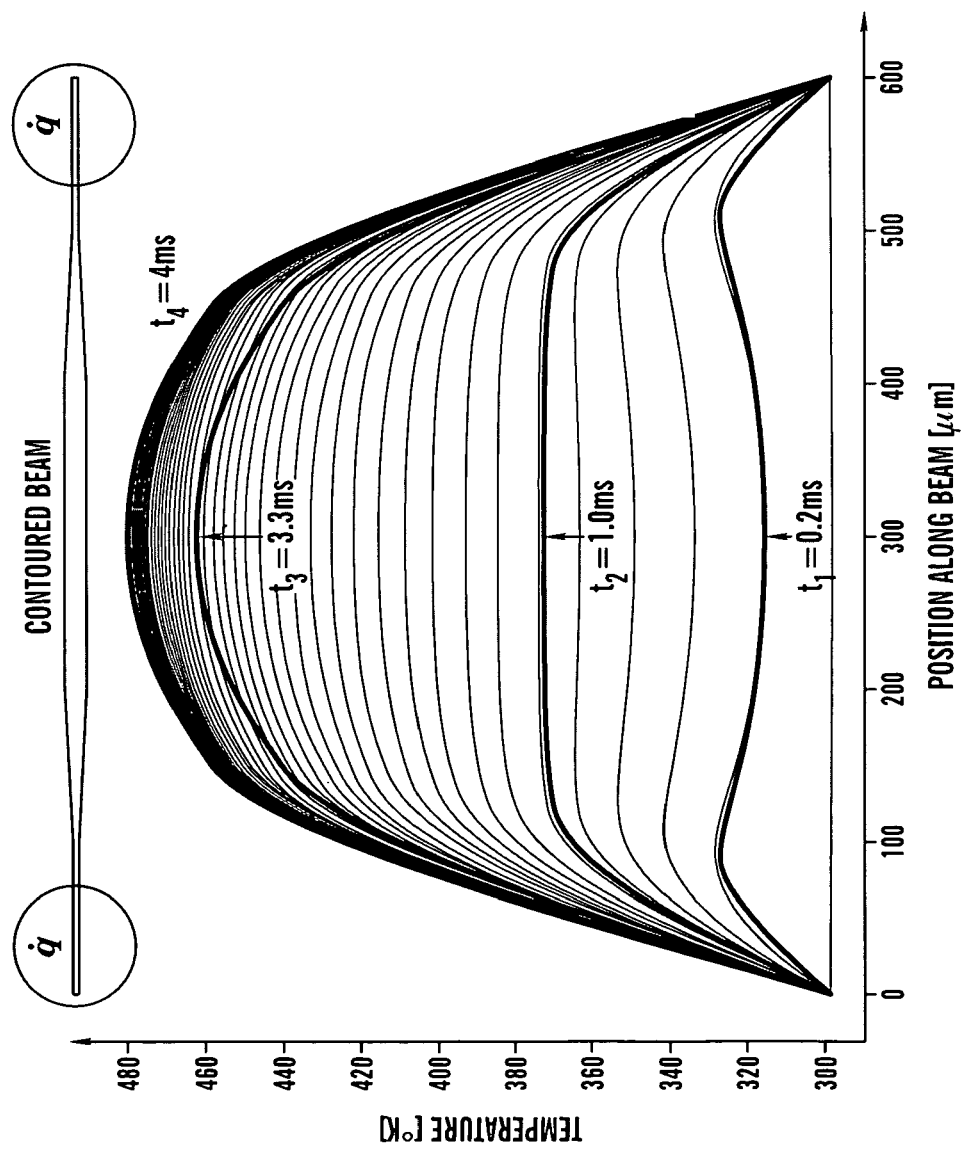
FIGS. 2A, 2B are graphical representations of temperature/heat profiles of contoured and straight TMAs subject to the same power input, respectively.
Figure 2B:
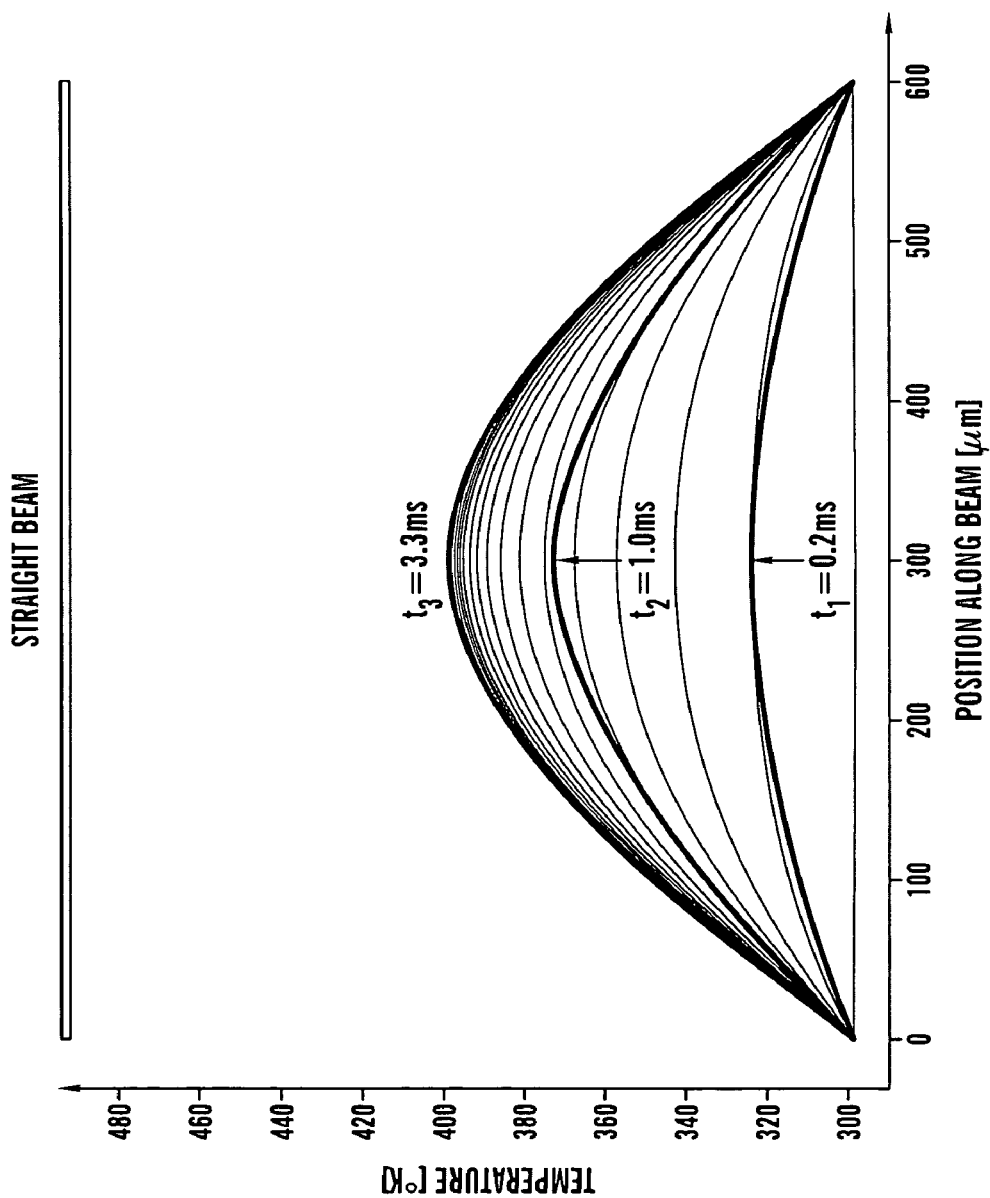

Turning now to FIGS. 2A, 2B, transient heating profiles of a contoured TMA 34 (FIG. 2A) and a straight TMA 30 (FIG. 2B) are respectively shown. In these examples, a constant current of 25 mA is supplied to both beams and the temporal change of the temperature profiles is plotted. The parameters used in the examples are listed in Table 2. While not wishing to be tied to a particular theory, it is believed that the differences between the temperature profiles of these two TMAs are due to inhomogeneous distributions of heat along the contoured TMA 34.

TABLE 2

Design parameters used in examples of FIGS. 2A and 2B.

| | Example A | Example B |
|---|---|---|
| Type | Contour | Constant cross-section |
| $L_S/L_L$ | 1 | N/A |
| $L/2L_L$ | 3 | N/A |
| $1/w'$ | 1/2 | 1 |
| $w_e$ | 8 μm | 8 μm |
| L | 600 μm | 600 μm |
| b | 30 μm | 30 μm |
| Driving current | 25 mA | |

In FIGS. 2A and 2B, the x-axis and y-axis represent the position and temperature along TMAs 34, 30, respectively. In both cases, the two ends of the beams are assumed to be attached to a heat sink maintained at room temperature. Starting from T=300° K (room temperature), each temperature profile is offset by a 0.2 milli-second time interval. By qualitatively comparing examples A and B, it is found that the contoured beam has a slightly larger thermal time constant, which is expected because the heat generated at both ends of the contoured TMA 34 would require some time to reach equilibrium state.

It is also found that the average temperature on the contoured beam rises faster than the straight beam, which indicates that for identical input/power, the contoured TMA has a higher forward stroke speed. Quantitative observation and calculations may be done based upon FIGS. 2A and 2B by calculating the different temperature profiles.

Another property of contoured beam 34 is that its temperature profile goes through three different stages as time progresses. At stage 1, the temperature on both ends of the contoured beam rises faster than in the central region and forms a concave-up profile (as more heat is generated on both ends), such as shown at $t_1$=0.2 ms. At stage 2, the heat accumulates at the central region, and there is a moment in time where the temperature profile becomes relatively "flat" on a rather wide mid-portion of the contoured beam, such as shown at $t_2$=1.0 ms. At stage 3, the system gradually reaches steady state and forms a uniform bell-shape temperature profile, such as shown at $t_3$=3.3 ms and $t_4$=4 ms.

It is also noted that the heating and cooling temperature profiles are different for a contoured beam 34. In the cooling process, it has been found that the temperature of beam 34 tends to decrease faster than the similar straight beam 30, which is somewhat counter-intuitive given the greater overall heat content of the contoured beam 34, as shown by the area under the curves of FIGS. 2A, 2B. It has been found that this faster cooling is provided by the relatively large temperature gradient at the ends of the beam relative to ground, provided by the contour, as shown by the relatively steep profile at the ends of the beam in FIG. 2A. Embodiments of the present invention use these unique heating/cooling characteristics in combination with a high speed pulsing approach to provide an improved TMA actuation system.

Pulsing Technique

Figure 3A:
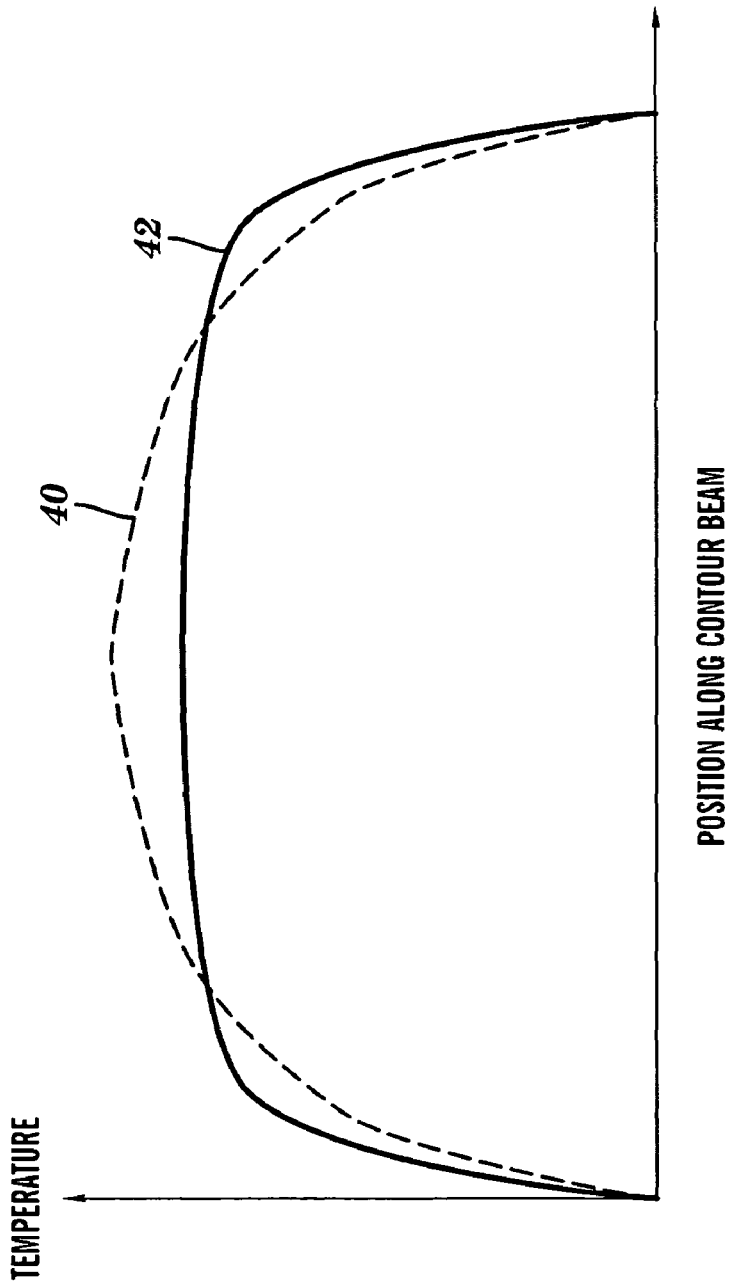
FIG. 3A is a graphical representation of temperature/heat profiles of a contoured TMA heated with a conventional pulse, and with a transient pulse for similar displacement in accordance with embodiments of the present invention.
Figure 3B:
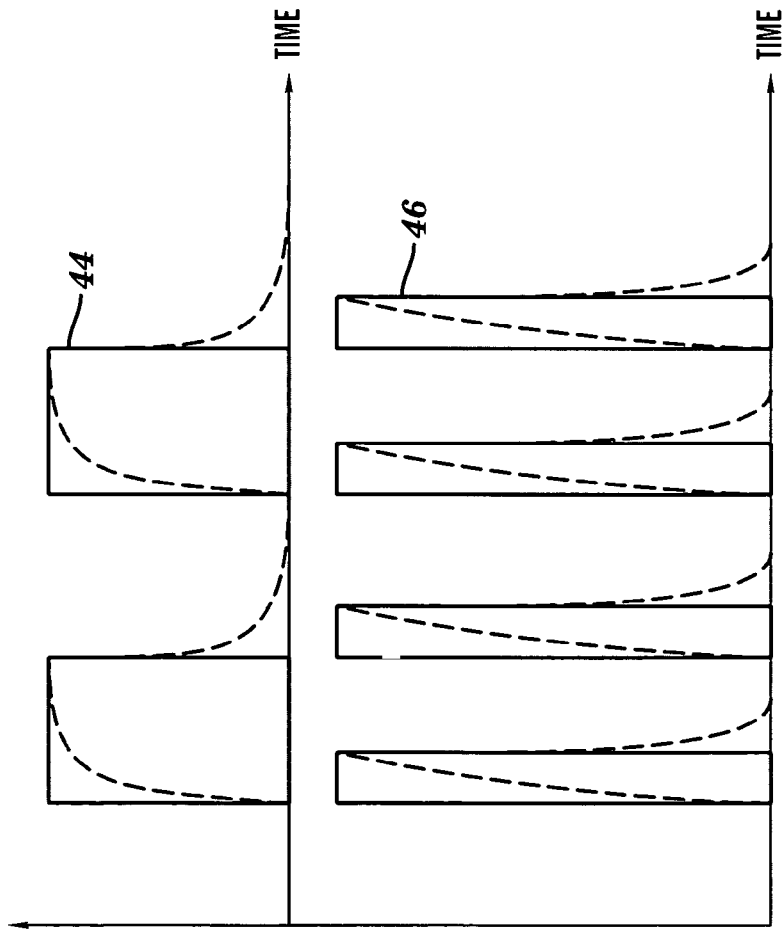
FIG. 3B is a graphical representation of conventional and transient pulses.

Referring now to FIGS. 3A and 3B, embodiments of the present invention use a short pulse actuation in which the aforementioned non-uniform heat generation characteristics of Joule heated beam 34 are used to re-shape the temperature distribution along the beam to form a relatively flat temperature profile, as shown in FIG. 3A. This flat temperature profile is provided by using transient pulses 46 to heat the contoured TMA 34 to stage 2 of its three-stage temperature profile.

FIG. 3A shows the temperature profiles 40, 42 of a contoured beam 34 respectively actuated with conventional steady state pulses 44 (FIG. 3B) that heat TMA 34 to its steady state "stage 3" profile, and transient, short pulses 46 (FIG. 3B) that heat TMA 34 to its transient "stage 2" profile.

Figure 6A:
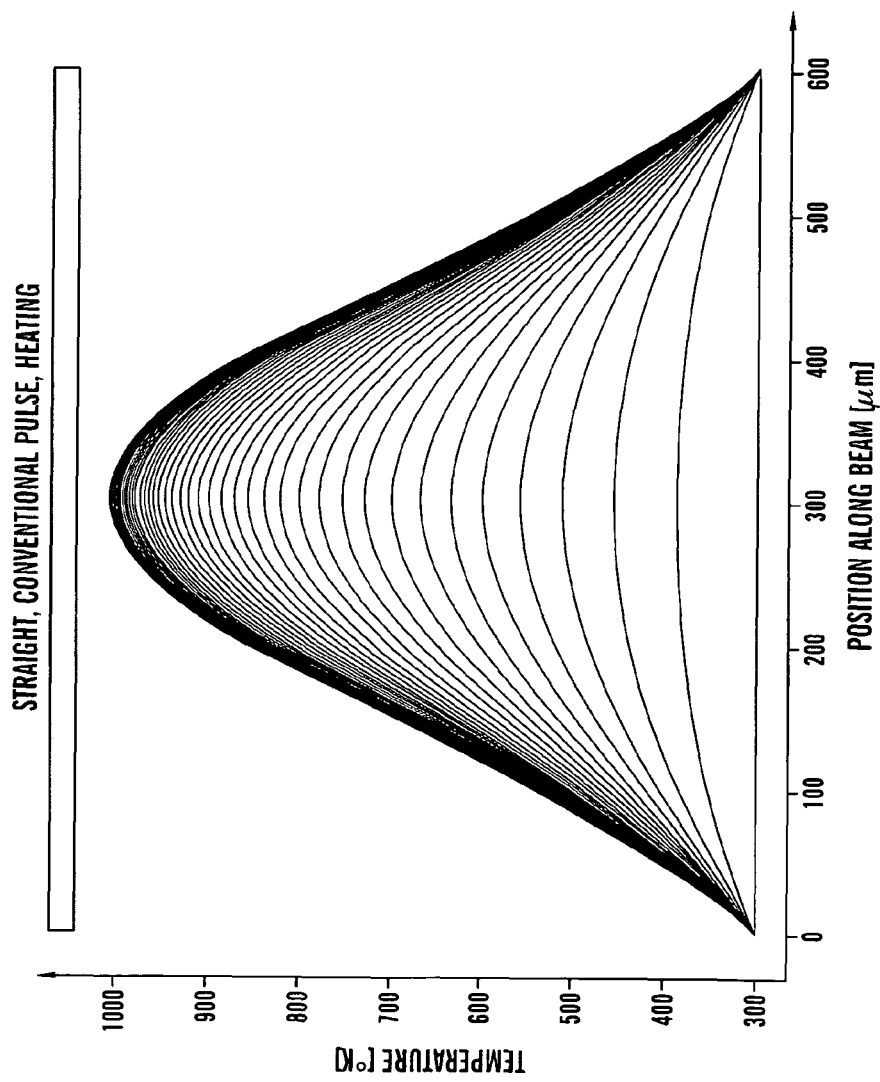
FIGS. 6A, 6B are graphical representations of heat profiles of a prior art TMA heated conventionally, during heating and cooling.

As shown in FIG. 3B, pulses 44 are referred to as steady state pulses since they tend to reach a plateau or horizontal peak prior to dropping. As mentioned hereinabove, these pulses 44 drive TMAs to a quasi-static state, i.e., steady state, for either a TMA 30 (as shown in FIG. 6A) or a TMA 34 in its "stage 2" (as shown at 40, FIG. 3A), and then let the actuators slowly cool down, returning to their original positions. Pulses 44 are, for example, conventionally used in a 50% duty cycle, such as shown in FIG. 3B. It is noted that advantages associated with embodiments of the present invention would not be realized by simply applying transient pulses 46 to conventional straight TMAs 30, since the TMAs 30 do not have three-stage temperature profiles, as discussed hereinabove.

Pulses 46 are referred to as transient pulses since they are still rising in amplitude (e.g., in current) and thus have not leveled off or plateaued, at the point at which they are terminated. In other words, the transient pulses are those having a voltage and current combination which, if enabled to reach steady state, would heat at least a portion (e.g., central portion) of the TMA beyond its predetermined operational temperature range. (In various embodiments, the predetermined operational temperature range is determined based on design requirements/constraints. However, a temperature closer to the failure temperature will typically increase the overall thermal efficiency. The failure temperature is defined as the temperature at which the modulus of the material (e.g. silicon), will change, e.g., decrease, which may ultimately cause the material to melt. In particular embodiments, the predetermined operational temperature is about 50-90 percent of the failure temperature of the material. Moreover, in some representative embodiments, the pulses 46 have an amplitude (e.g., voltage or current) which is at least about, for example, 1.25 to 1.5 times the level required to heat the TMA to its predetermined operational temperature range, in the event the pulses were permitted to reach their steady state.

It is noted that although square waves are used as short pulses 46 in the previous examples, the short pulse signals are not limited to square waves. For example, the pulse 46 may be combined with other nominally any conventional signal control/conditioning/preshaping techniques to achieve desired dynamic performance. The spirit of the short or transient pulse is that its "average amplitude" and "average pulse width" is respectively larger and smaller than that of the conventional steady state signal.

It should be noted that while profile 40 is steady state, the flat temperature profile 42 is a transient state. As mentioned above, this transient state profile 42 ("stage 2" of TMA 34) is steeper at the ends of the beam, denoting a relatively high temperature gradient. The high gradient enables more heat to be removed from the contoured beam 34 to the heat sink, to reduce overall cooling time.

Thus, as compared to operation of a conventional straight TMA 30, the transient pulse 46 activation of this approach enables a contoured three-stage TMA 34 to heated to its transient "stage 2" temperature profile, to provide a high temperature gradient on the two ends of beam 34 to increase the cooling speed, increased maximum displacement, faster displacement, and decreased energy consumption.

The following illustrative examples demonstrate certain aspects and embodiments of the present invention, and are not intended to limit the present invention to any one particular embodiment or set of features.

EXAMPLES

Heating and cooling profiles of exemplary contoured TMAs 34, using both short and conventional pulses, are described in the following Examples, with reference to FIGS. 4-6.

A Finite Element Analysis (FEA) program (COMSOL) was used to quantify some of the benefits that may be obtained through the contoured beam and pulsing technique of the present invention. Heating and cooling profiles of a Joule heated contoured beam 34 actuated with a short pulse signal are respectively shown in FIGS. 4A, 4B, while temperature profiles of the same beam actuated with a conventional steady state signal are shown in FIGS. 5A, 5B. As a Control, heating and cooling profiles of a conventional straight Joule heated beam 30 driven by a conventional signal is simulated, with heating and cooling profiles shown in FIGS. 6A, 6B, respectively. In these examples, the conventional straight beam 30 has a constant cross section and the same volume and length as the contoured beams 34. The design parameters for these beams and pulses are listed in Table 3, and the results are summarized in comparison to the conventional approach, in Table 4.

TABLE 3

Design parameters used in FIGS. 4A-6B.

Figure 4A:
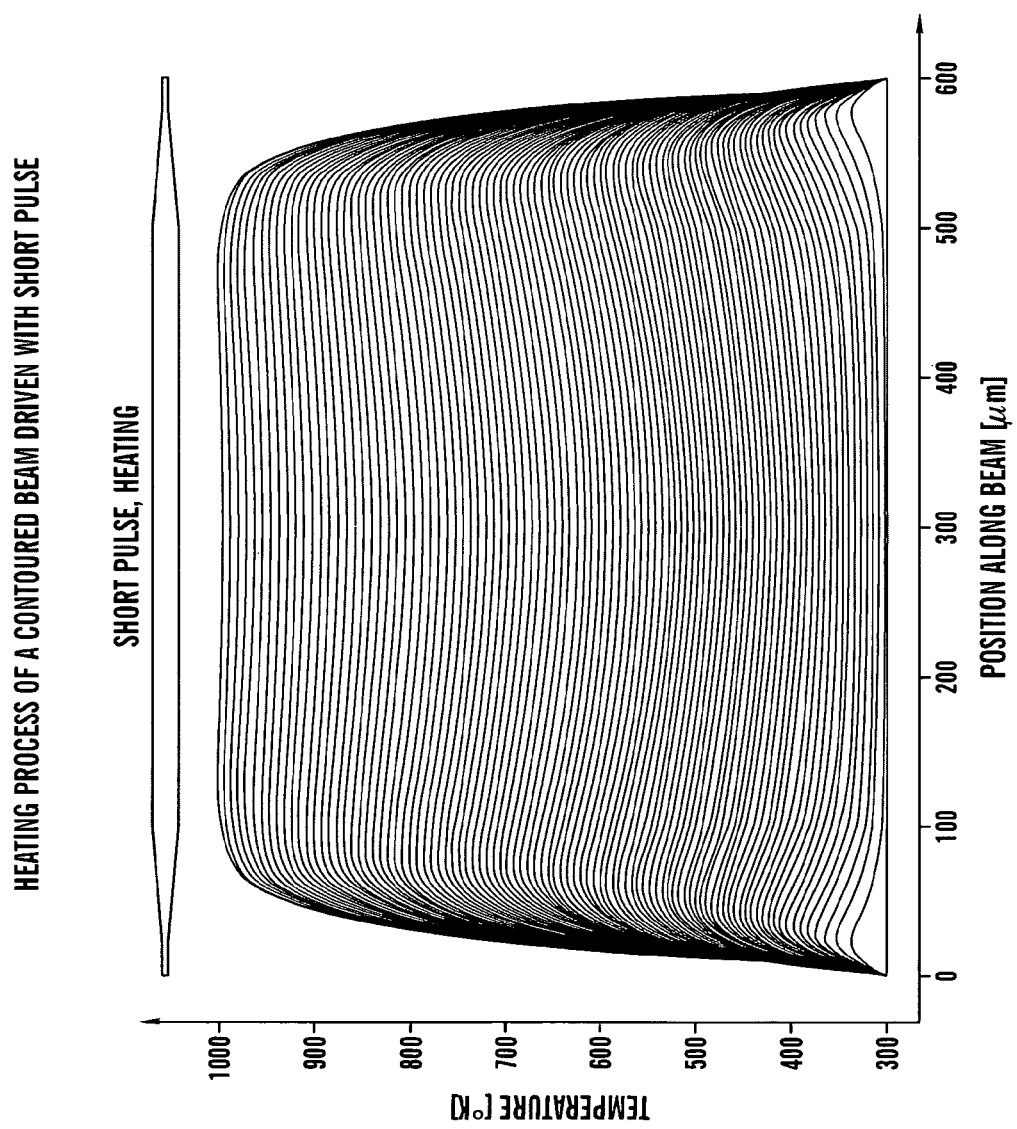
FIGS. 4A, 4B are graphical representations of temperature/heat profiles of a contoured TMA heated in accordance with embodiments of the present invention, during heating and cooling.
Figure 4B:
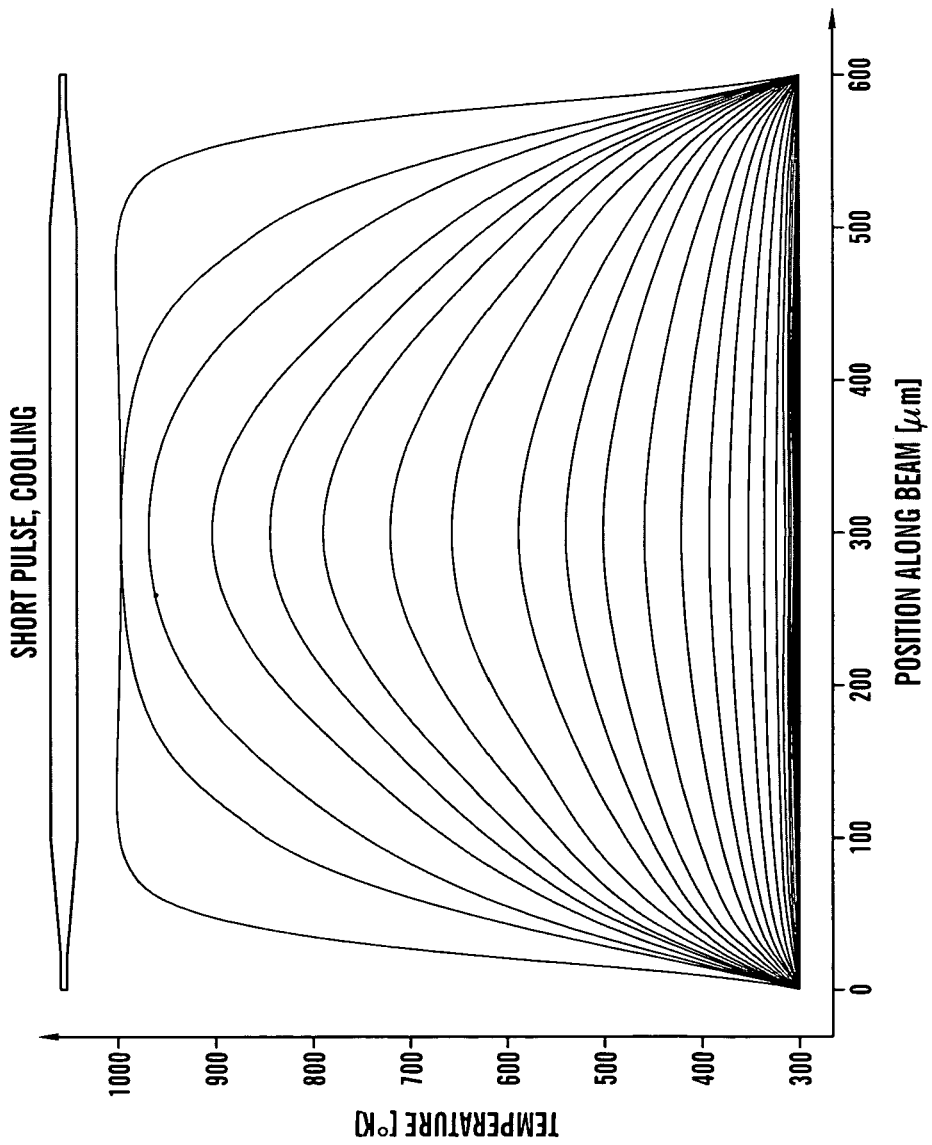
Figure 5A:
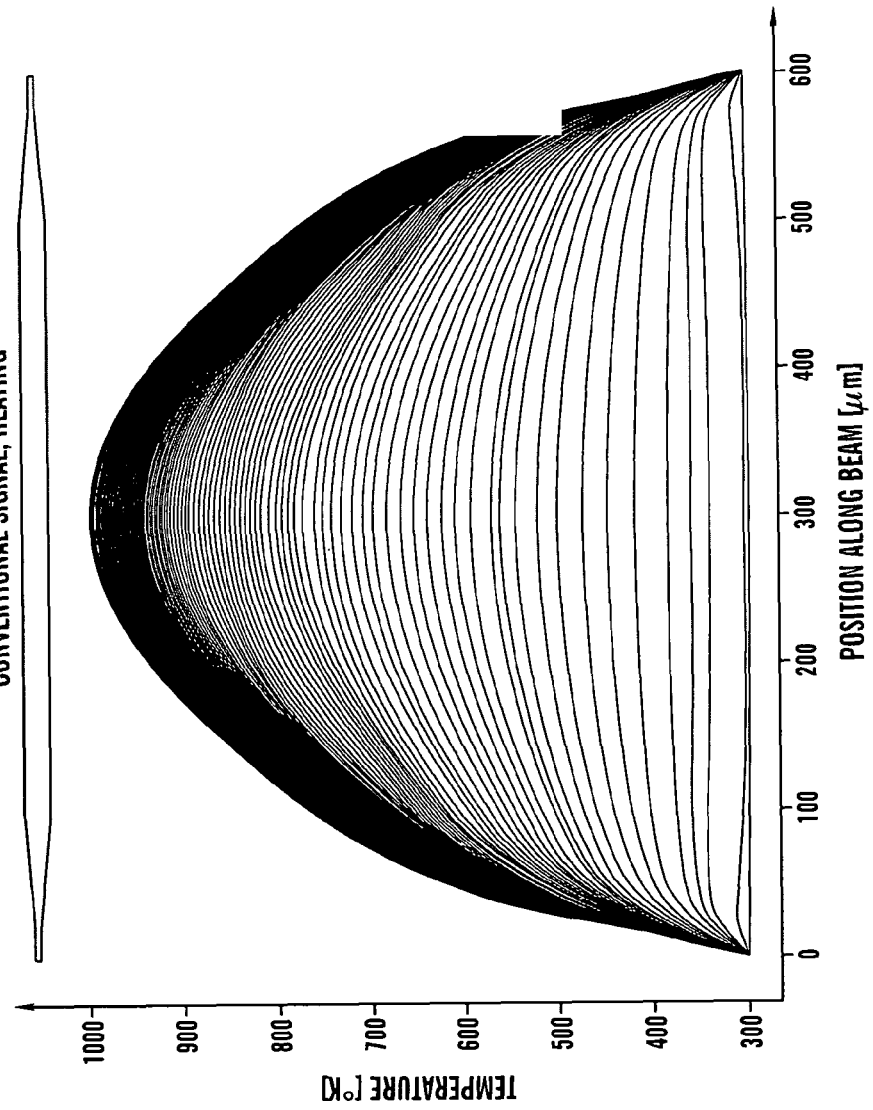
FIGS. 5A, 5B are graphical representations of temperature/heat profiles of a contoured TMA heated conventionally, during heating and cooling.
Figure 5B:
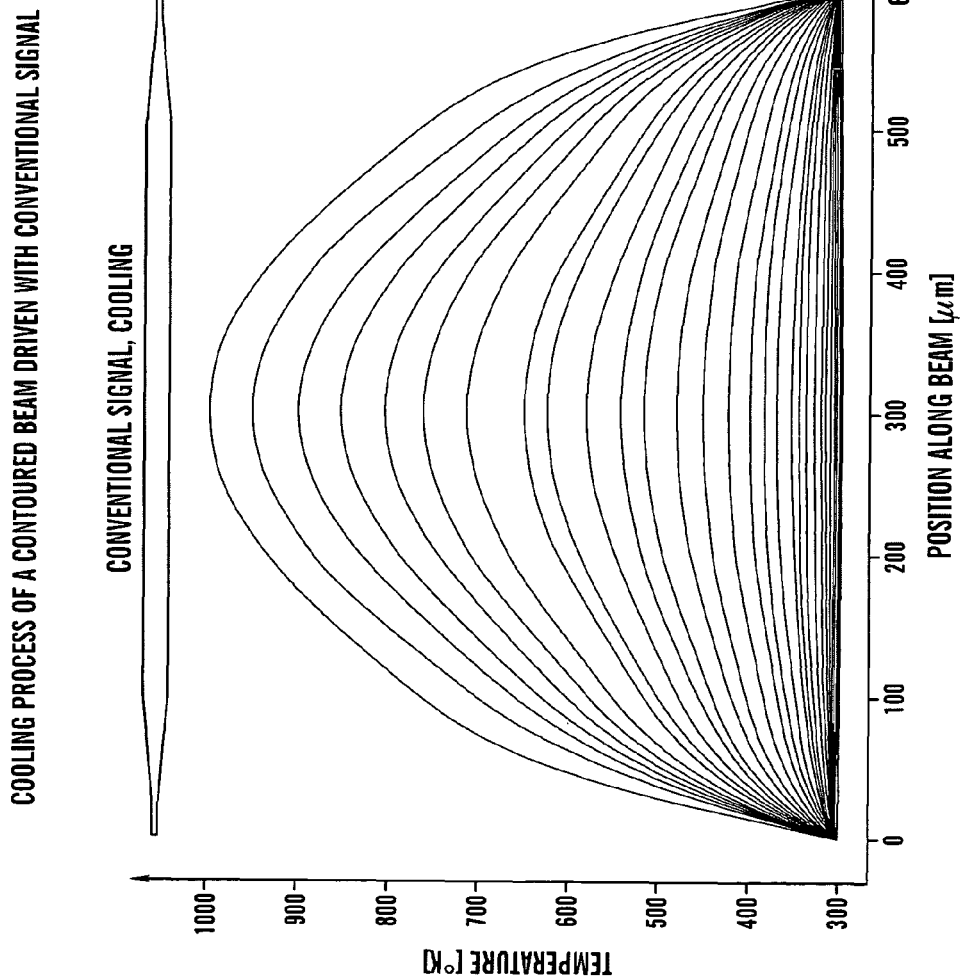
Figure 6B:
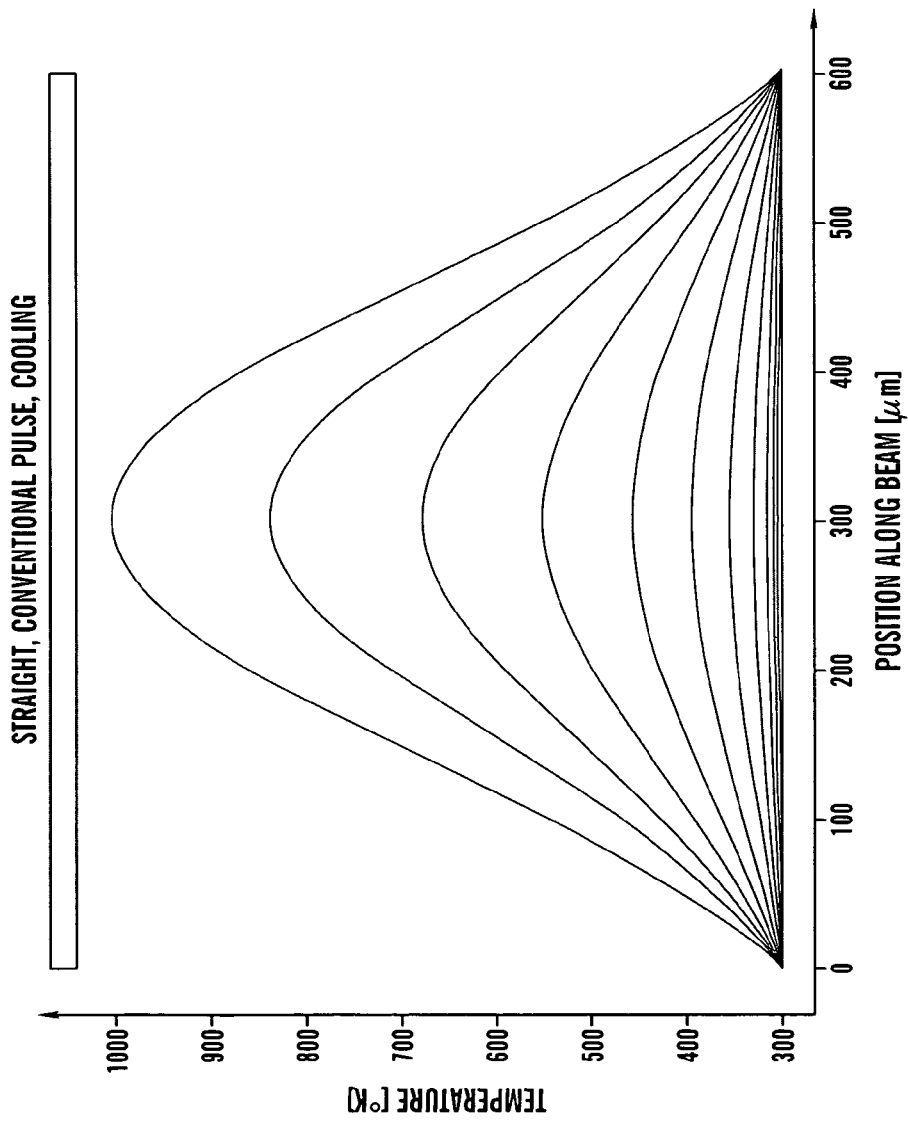

| | FIGS. 4A, 4B | FIGS. 5A, 5B | FIGS. 6A, 6B |
|---|---|---|---|
| Type | Contour beam | | Straight beam |
| $L_S/L_L$ | 1/10 | | N/A |
| $L/2L_L$ | 3/2 | | N/A |
| $1/w' = w_L/w_S$ | 5 | | 1 |
| L (length of the beam) | 600 μm | | 600 μm |
| B (height of the beam) | 30 μm | | 30 μm |
| Signal type | Short pulse | Conventional | Conventional |
| Signal value | 54 mA | 27 mA | 35 mA |
| Pulse width | 0.94 ms | 30 ms | 30 ms |
| Command max. temp. | 1000°K | 1000°K | 1000°K |
| Note | Time increment = 10 μs | | |

In these Examples, beams 34, 30 are fabricated from silicon, with a peak safe operating temperature set to be 1000° K. As shown in FIG. 4A, a substantially flat temperature profile was achieved at 1000° K. It is noted that almost 80% of the Joule heated contoured beam may be maintained at 1000° K as compared to a single point at 1000° K for both the contoured beam 34 and straight beam 30 when driven with conventional signals as respectively shown in FIGS. 5A and 6A.

As shown in FIG. 4B, the temperature at both ends of the contoured, short pulsed beam dropped faster than those of the other examples (FIGS. 5B, 6B), due to the aforementioned high temperature gradient.

As shown in FIGS. 6A, 6B, the temperature profiles of the constant cross-section beam 30, driven with a conventional signal, deviate from parabolic shapes. These conventional temperature profiles tend to be inferior to parabolic profiles as they yield a lower average temperature than parabolic profile at a given $T_{MAX}$ ($T_{MAX}$=1000° K in this Example). The instant inventors attribute this effect to the fact that the thermal conductivity for silicon is a function of temperature and tends to decrease relatively quickly as the temperature increases. In terms of actual beam elongation or TMA displacement, the straight beam TMA has been shown to yield worse performance than the inventive TMAs because the value of silicon's coefficient of thermal expansion at 1000° K is two times higher than the value at room temperature. The combined effects of the contoured beam with short pulse signal of the present invention have been shown to generate 70% more extension in beam length ($\Delta_T$) than a straight beam, with a $T_{MAX}$ on both beams of 1000° K.

As shown in Table 4, it is observed that a simultaneous 28% enhancement in stroke, 11% reduction in cooling time, and 70.9% reduction in required actuation energy is provided (on the same contoured beam 34) when using the transient short pulse signal. Moreover, the same displacement provided by the conventional beam/signal at $T_{MAX}$ of 1000° K may be achieved using the inventive beam and pulsing approach at a $T_{MAX}$ of only 850° K. Also, in this scenario, the time required for cooling and the reduction in power are further enhanced by 23% and 73% respectively.

Two parameters, signal (current) amplitude ($I_P$) and pulse width ($t_P$), need to be determined for the short pulse. The example of FIG. 4A will be used here to demonstrate how $I_P$ and $t_P$ were found. In FIG. 4A, a desired temperature is set at 1000° K, and the objective is to find the current, $I_P$, and $t_P$ so that the temperature at the center (i.e., at x=0) of beam 34 is substantially equal to the temperature close to the ends (i.e., at x=±L/2) of the contoured beam at time $t_P$. As shown in Equation (03-06), $I_P$ and $t_P$ may be found with the described objective and a proper initial condition (I.C.) and boundary conditions (B.C.).

$$\frac{\partial}{\partial x}k(T)\frac{\partial T}{\partial x} + r(x) \cdot \frac{I_P}{A(x)} = \rho \cdot C_P \frac{\partial T}{\partial t} \quad (03)$$

$$B.C. T(x = L, t_0 = 0) = T(x = 0, t_0 = 0) = 300 \text{ K} \quad (04)$$

$$I.C. T(x, t_0 = 0) = 300 \text{ K} \quad (05)$$

$$\text{Objective: } T(x_1, t_P) = T(x_2, t_P) = 1000 \text{ K} \quad (06)$$

In another example, a series of parallel TMAs 34 were used in an endoscopic scanner for a two-photon endomicroscope having a conventional gradient index (GRIN) lens 50. It is noted that TMAs 34 are particularly suitable for in vivo endoscopic applications due to their combination of relatively high force and low driving voltage. In this example, an active silicon optical bench 52, shown in FIGS. 7A, 7B, contains flexure bearings 54 and contoured TMAs 34 that control the z motion of the gradient index (GRIN) lens 50 and the angular motion, θx, of the lens 50 for in-plane 2D scanning.

Figure 7A:
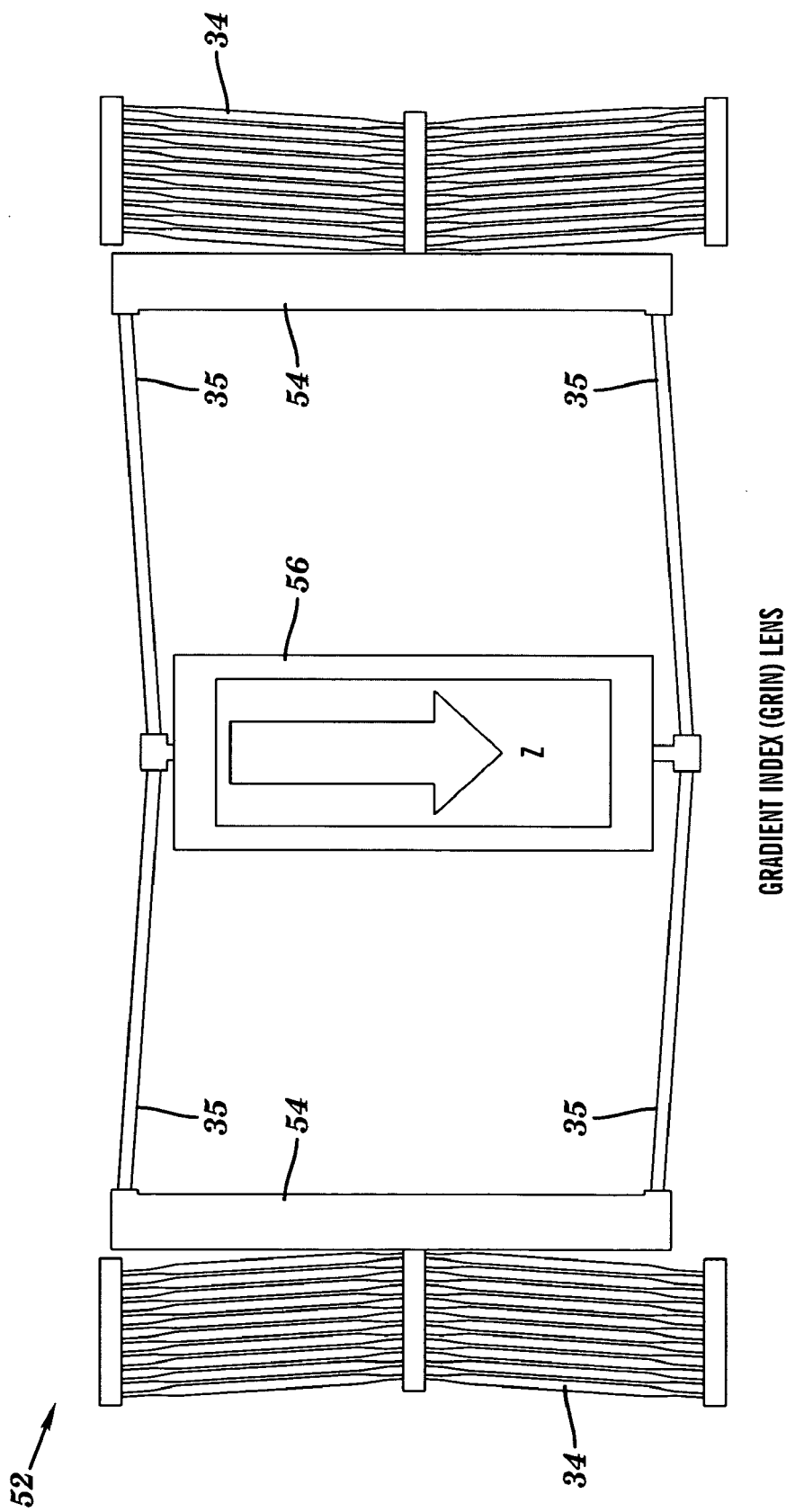
FIGS. 7A, 7B are schematic plan and perspective views of a representative application using embodiments of the present invention.
Figure 7B:
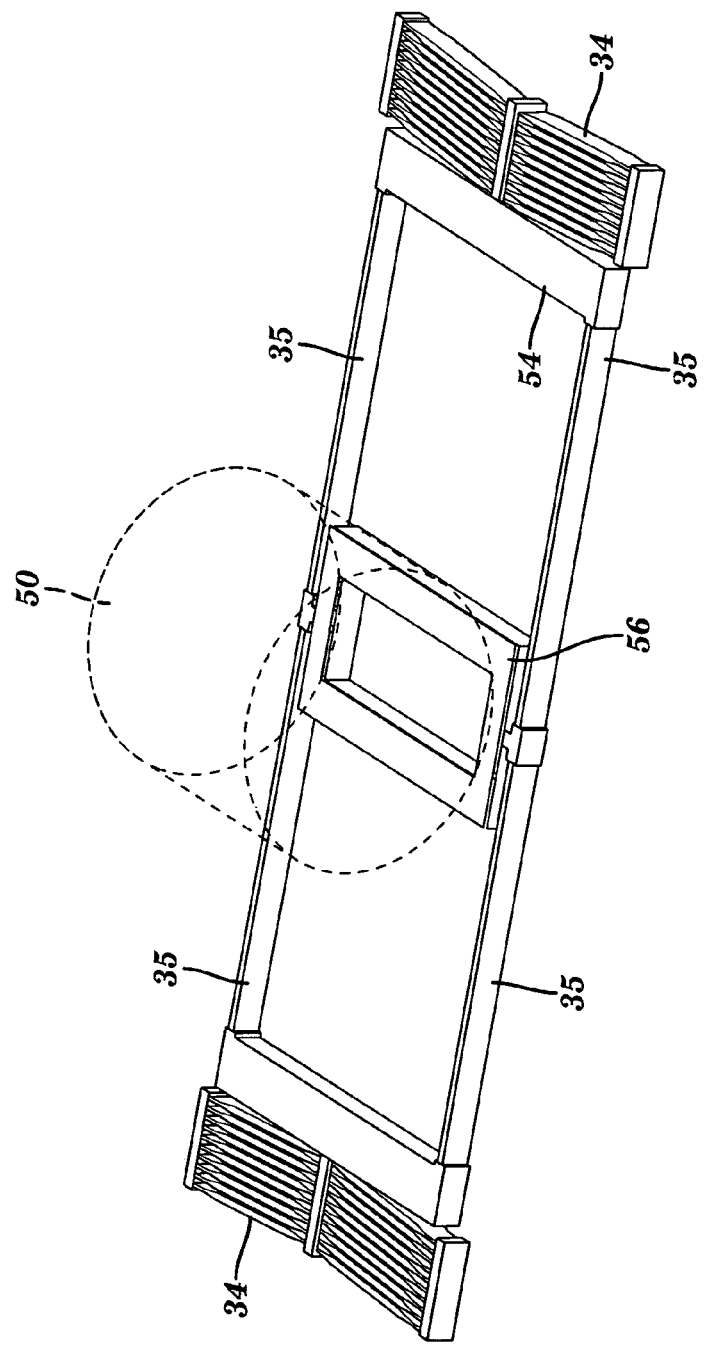

As shown in FIGS. 7A, 7B, the GRIN lens 50 is disposed on a shuttle 56, which is fabricated integrally with the in-plane contoured chevron TMAs 34 (and chevron flexures 35), e.g., by microfabrication as discussed hereinbelow. The optical bench 52 provides micrometer level precision alignment for small optical elements. Moreover, as shown, it is sym-

TABLE 4

Summary of performance of examples in FIGS. 4A-6B.

|  | FIGS. 4A, 4B | FIGS. 5A, 5B | FIGS. 6A, 6B |
| --- | --- | --- | --- |
| Type |  | Contoured | Straight |
| Signal type | Short pulse | Conventional | Conventional |
| Rise time | 0.853 ms | 13.80 ms | 6.66 ms |
| Fall time | 3.02 ms | 3.40 ms | 1.60 ms |
| Elongation | 2.058 μm | 1.605 μm | 1.214 μm |
| Stroke enhancement [%] | ↑ 28.2% | 1 | ↓ 24.4% |
| Normalized forward speed enhancement | ↑ 19.8X | 1 | ↑ 1.5X |
| Normalized returning speed enhancement | ↑ 1.5X | 1 | ↑ 1.6X |
| Normalized energy consumption [%] | ↓ 70.9% | 1 | ↑ 68.0% |
| Note |  | Time increment = 10 μs |  |

Pulsed Signal Determination

A systematic approach may be used to determine an optimal short pulse for a given contoured beam at a desired flat (e.g., maximum) temperature. If too much power is supplied in a short time for a contoured beam (e.g., if the transient pulse is permitted to approach steady state), the beam may fail (burn out), e.g., at the ends of the beam before it reaches a flat temperature profile. If too little power is supplied, however, the temperature profile will become flat at a lower than optimal temperature, at which temperature some of the benefits of the present invention may not be achieved.

metrical, including a two-stage chevron amplification mechanism driven by symmetrical chevron TMA trains 34 actuatable in the direction perpendicular to the Z direction. The chevron flexures 35 that connect the TMA trains 34 and the GRIN lens shuttle 56 further amplify the motion provided from the TMA trains 34. The symmetric design provides precision motion guidance and reduced parasitic motion for the GRIN lens 50.

Figure 8A:
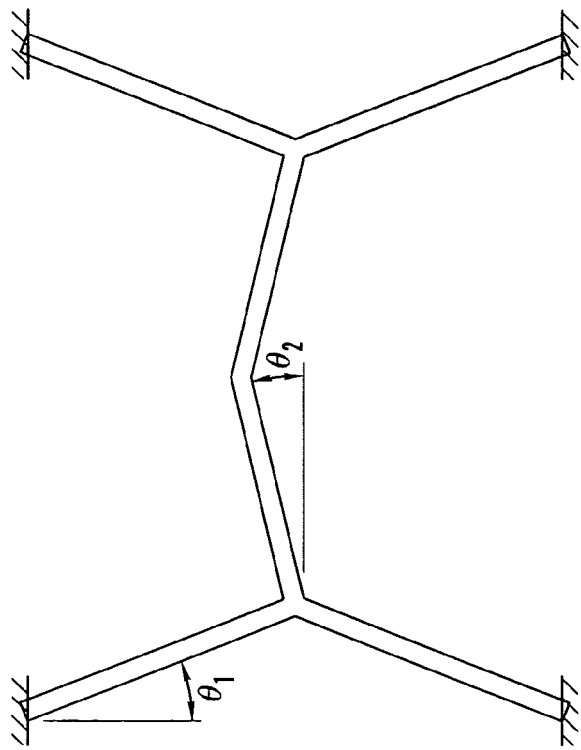
FIGS. 8A, 8B show transmission ratio surface plots as a function of $\Theta_1$, $\Theta_2$ and the number of parallel TMAs.
Figure 8B:
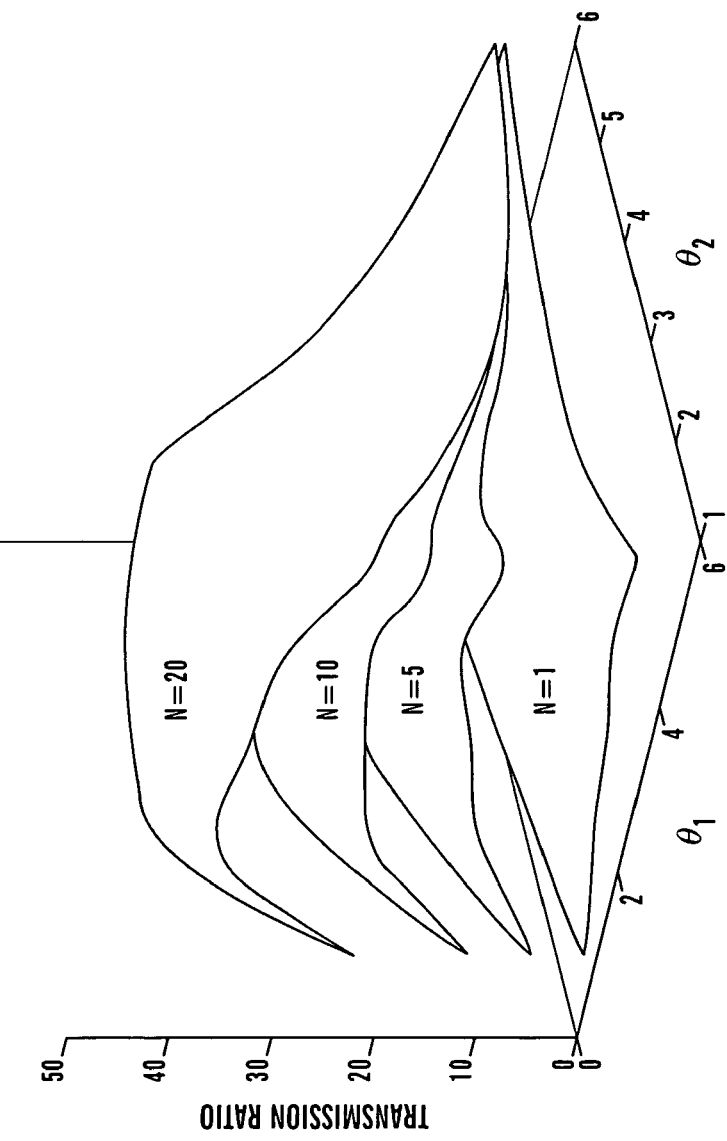

The transmission ratio, which is defined as the output displacement over input displacement, of the two-stage chevron mechanism was optimized by mechanically matching the axial and lateral stiffness of the individual chevron flexures, by disposing them at predetermined angles $\theta_1$ and $\theta_2$, as shown in FIG. 8A. FIG. 8B presents the surface plot of transmission ratio as functions of $\theta_1$ and $\theta_2$ for different numbers of contoured TMAs. Based on this plot, angles $\theta_1$ and $\theta_2$ and the number of TMAs 34 for a particular application may be selected.

Figure 9:
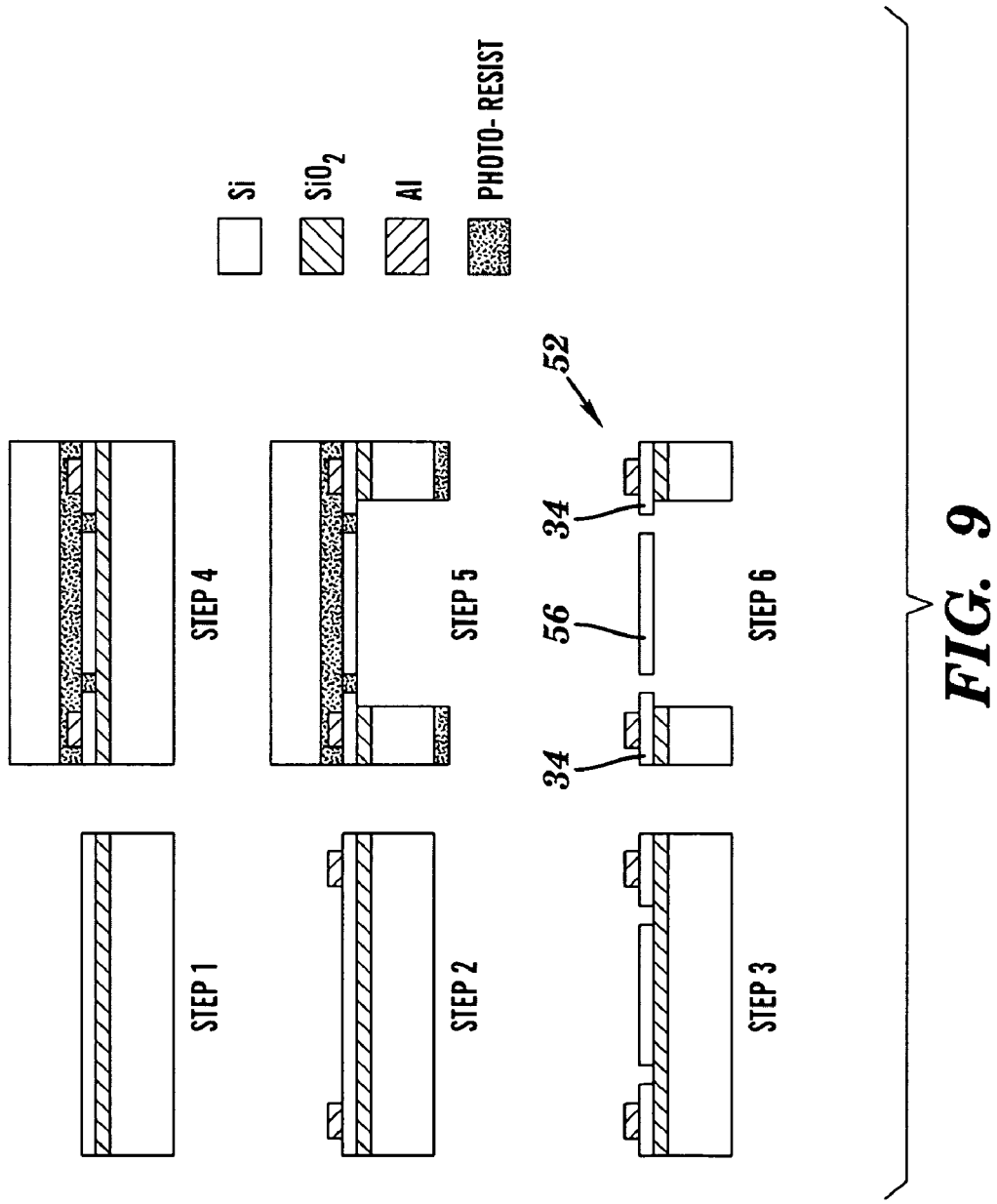
FIG. 9 is a schematic representation of various exemplary fabrication steps of an embodiment of the present invention.

Turning now to FIG. 9, an exemplary method of fabricating embodiments of the present invention is shown and described. This exemplary methodology may be used to fabricate any of the embodiments described herein, with particular reference to the 2D active silicon optical bench 52.

Step 1: 150 mm SOI wafer includes three layers: Silicon handling wafer (500 μm)-Silicon Dioxide (2 μm)-Silicon device layer (200 μm).

Step 2: Aluminum electrical contact pads are patterned on the wafer.

Step 3: The mechanism-actuator geometry is etched through the device layer via deep reactive ion etching (DRIE).

Step 4: The wafer is mounted to a quartz handling and support wafer.

Step 5: A back-side DRIE process creates access to the silicon dioxide layer.

Step 6: The quartz wafer is removed from the device wafer. A concentrated vapor Hydrofluoric acid is used to release the mechanism 52 including shuttle 56 and actuators 34.

It should be understood that any of the features described with respect to one of the embodiments described herein may be similarly applied to any of the other embodiments described herein without departing from the scope of the present invention.

In the preceding specification, the invention has been described with reference to specific exemplary embodiments for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

Having thus described the invention, what is claimed is:

1. A thermomechanical actuation system comprising:
an elongated thermomechanical actuator (TMA);
the TMA having a contour, wherein electrical resistance at a mid-portion of the TMA is less than at end portions thereof;
the TMA having a predetermined peak operational temperature range;
a pulse generator electrically coupled to the TMA;
the pulse generator configured to supply excitation pulses to the TMA;
the excitation pulses being transient, wherein each pulse is terminated prior to reaching a steady state amplitude, while having sufficient energy to heat the TMA to the predetermined operational temperature range; and
wherein the pulse generator is configured to supply excitation pulses predetermined to provide the TMA with a substantially flat temperature profile along at least the middle 30% of the TMA, with a higher temperature at the middle 30% than at opposite end portions of the TMA.

2. The system of claim 1, wherein the predetermined operational temperature range is at least about 50 percent to about 100 percent of a maximum operating temperature of the TMA.

3. The system of claim 2, wherein the predetermined operational temperature range is up to about 90 percent of the failure temperature of the TMA.

4. The system of claim 1, wherein the contour comprises a non-uniform transverse dimension, in which a transverse dimension at a mid-portion of the TMA is greater than a transverse dimension at either end of the TMA.

5. The system of claim 4, wherein the contour comprises a non-uniform cross-sectional area, in which a transverse cross-sectional area at a mid-portion of the TMA is greater than a transverse cross-sectional area at either end of the TMA.

6. The system of claim 1, wherein the contour comprises a non-uniform material composition.

7. The system of claim 6, wherein dopants are added to portions of the TMA.

8. The system of claim 1, wherein each of the excitation pulses is configured to have a sufficient energy level so that if permitted to reach steady state, would heat the TMA beyond the predetermined operational temperature range.

9. The system of claim 8, wherein the energy level' comprises a combination of voltage and current.

10. The system of claim 8, wherein the energy level is at least about 1.25 to 1.5 times that capable of heating the TMA to its predetermined operational temperature range, if the pulse is permitted to reach steady state.

11. The system of claim 10, wherein the TMA is microfabricated.

12. The system of claim 11, wherein the TMA is fabricated from silicon.

13. The system of claim 1, wherein the TMA has a three-stage temperature profile, forming a concave-up profile at a stage 1, a substantially flat profile at a stage 2, and a concave down profile at a stage 3.

14. A method of thermomechanical actuation, the method comprising:
(a) providing an elongated thermomechanical actuator (TMA), having a contour, wherein electrical resistance at a mid-portion of the TMA is less than at end portions thereof, the TMA having a predetermined peak operational temperature range;
(b) electrically coupling a pulse generator to the TMA;
(c) configuring the pulse generator to supply excitation pulses to the TMA;
(d) configuring the excitation pulses to be transient, wherein each pulse is terminated prior to reaching a steady state amplitude;
(e) providing the excitation pulses with sufficient energy to heat the TMA to the predetermined operational temperature range; and wherein the pulse generator is configured to supply excitation pulses predetermined to provide the TMA with a substantially flat temperature profile along at least the middle 30% of the TMA, with a higher temperature at the middle 30% than at opposite end portions of the TMA.

15. The method of claim 14, wherein the predetermined operational temperature range is at least about 50 percent to about 100 percent of a maximum operating temperature of the TMA.

16. The method of claim 15, wherein the predetermined operational temperature range is up to about 90 percent of the failure temperature of the TMA.

17. The method of claim 14, wherein said providing (a) comprises providing a TMA having a contour in the form of a non-uniform transverse dimension, in which a transverse dimension at a mid-portion of the TMA is greater than a transverse dimension at either end of the TMA.

18. The method of claim 17, wherein said providing (a) comprises providing a TMA having a contour in the form of a non-uniform cross-sectional area, in which a transverse cross-sectional area at a mid-portion of the TMA is greater than a transverse cross-sectional area at either end of the TMA.

19. The method of claim 14, wherein said providing (a) comprises providing a TMA having contour in the form of a non-uniform material composition.

20. The method of claim 19, wherein said providing (a) comprises providing a TMA having dopants are added to portions thereof.

21. The method of claim 14, wherein said providing (e) comprises configuring each of the excitation pulses so that if permitted to reach steady state, would heat the TMA beyond the predetermined operational temperature range.

22. The method of claim 21, wherein said configuring each of the excitation pulses comprises configuring voltage and current.

23. The method of claim 21, wherein said providing (e) comprises configuring each of the excitation pulses so that if permitted to reach steady state, would have an energy level of at least about 1.25 to 1.5 times that capable of heating the TMA to its predetermined operational temperature range.

24. The method of claim 23, wherein the TMA is micro-fabricated.

25. The method of claim 24, wherein the TMA is fabricated from silicon.

* * * * *